United States Patent [19]

Haagensen, Jr.

[11] Patent Number: 5,648,224
[45] Date of Patent: Jul. 15, 1997

[54] METHOD OF DETERMINING THE RISK OF BREAST CANCER DEVELOPMENT

[76] Inventor: Darrow E. Haagensen, Jr., 8120 Timberlake Way, Sacramento, Calif. 95823

[21] Appl. No.: 515,146

[22] Filed: Aug. 15, 1995

[51] Int. Cl.$^6$ .......................... G01N 33/53; G01N 33/574
[52] U.S. Cl. ................. 435/7.23; 436/64; 436/813
[58] Field of Search ................. 435/7.23; 436/64, 436/813

[56] References Cited

U.S. PATENT DOCUMENTS

| | | | |
|---|---|---|---|
| 4,229,426 | 10/1980 | Haagensen, Jr. | 424/1 |
| 4,440,863 | 4/1984 | Haagensen, Jr. | 436/539 |
| 4,452,904 | 6/1984 | Haagensen, Jr. | 436/545 |

OTHER PUBLICATIONS

Vandewalle, et al., *Biochimie*, vol. 68, 649–656, 1986.
Cassoni et al., *Int. J. Cancer*, 60: 216–220 (1995).
Bodian et al., *Cancer Det. Prev.*, 16: 7–15 (1992).
Haagensen et al., *Br. Cancer Res. Treat.*, 23: 77–86 (1992).
Dejardin et al., *J. Mol. Endocrinology*, 7:105–112 (1991).
Bundred et al., *Brit. J. Cancer*, 64: 953–955 (1991).
Ciatto et al., *Eur. J. Cancer*, 26: 555–557 (1990).
Haagensen et al., *Ann. N.Y. Acad. Sci.*, 586: 161–173 (1990).
Myal et al., *Somatic and Mol. Genetics*, 15: 256–270 (1989).
Simard et al., *Mol. Endocrinology*, 3:694–702 (1989).
Wellings et al., *Hum. Path.*, 18–381–386 (1987).
Haagensen, Diseases of the Breast, 3rd ed., WB Saunder Publ; 250–266 (1986).
Mazoujian et al., *Am. J. Pathol.*, 110: 105–112 (1983).
Jones et al., *Brit. J. Surg.*, 67: 669–671 (1980).
Harrington et al., *Breast*, 7: 13–17 (1980).
Haagensen et al., *J. Natl. Cancer Inst.* 62: 239–247 (1979).
Chalbos et al., *Cancer Res.*, 47: 2787–2792 (1987).
Haagensen et al., *Diseases of the Breast*, 3rd ed., WB Sauder Publ; 474–500 (1986).

*Primary Examiner*—Toni R. Scheiner
*Attorney, Agent, or Firm*—Felfe & Lynch

[57] ABSTRACT

This invention relates to a method of determining, in a subject having active breast gross cystic disease, the risk of future breast cancer development. The level of glycoprotein GCDFP-15 in the plasma is measured at the time of cyst aspiration in order to provide an indication as to the likelihood of future breast cancer development.

10 Claims, No Drawings

METHOD OF DETERMINING THE RISK OF BREAST CANCER DEVELOPMENT

FIELD OF THE INVENTION

This invention relates to a method of assessing the risk of breast cancer development. More specifically, this invention relates to a method of determining the risk of future breast cancer development in a subject with active breast gross cystic disease. The level of glycoprotein GCDFP-15 in the plasma of said subject is measured in order to provide a prognosis for breast carcinoma development.

BACKGROUND OF THE INVENTION

Human breast gross cystic disease is a benign breast condition common in adult middle-aged women (Haagensen, *Diseases of the Breast*, 3rd ed., WB Saunders Publ., pp. 250–266 (1986)). Gross cysts evolve from microcystic apocrine metaplasia, which occurs in the terminal ductal lobular units of the breast (Wellings et al., *Hum. Path.*, 18:381–386 (1987)). The cause of apocrine microcyst transformation into macrocysts is unknown. However, there is evidence that such transformation is a hormonally mediated event. Gross cystic disease first appears in women in their 20's and increases in frequency up to the 40–50 age range, and then essentially disappears as a disease process after menopause (Haagensen, 1986, supra).

Breast gross cystic disease is confirmed by aspiration of cyst fluid. It has been found that as a population, women who have gross cystic disease have an increased risk of developing breast carcinoma (see Jones et al., *Brit. J. Surg.*, 67:669–671 (1980); Harrington et al., Breast, 7:13–17 (1980); Ciatto et al., *Eur. J. Cancer*, 26:555–557 (1990); Bundred et al., *Brit. J. Cancer*, 64:953–955 (1991); and Bodian et al., *Cancer Det. Prev.*, 16:7–15 (1992)). The fluid contained within breast gross cysts has been analyzed for a number of components, and has been found to be a unique secretion. The major component proteins have been identified (Haagensen et al., *J. Natl. Cancer Inst.*, 62:239–247 (1979)). One of these component proteins, termed GCDFP-15 for a 15K dalton monomer sized glycoprotein, has been investigated as a marker protein with regard to its circulating blood levels in various clinical situations (see Haagensen et al., 1979, supra; Haagensen et al., 1986, supra, pp. 474–500; and Haagensen et al., *Ann. N.Y. Acad. Sci.*, 586:161–173 (1990)). GCDFP-15 blood levels in "normal" post-menopausal women averages 17 ng/ml.

GCDFP-15 protein has been well characterized with regard to its amino acid structure and the location of its gene on chromosome 7 (see Haagensen et al., 1986, supra; and Myal et al., *Somatic and Mol. Genetics*, 15:256–270 (1989)). GCDFP-15 is a normal constituent protein of all apocrine gland cells (normal and metaplastic), and of some exocrine glands with apocrine features (serous cells of mandibular salivary glands and the minor salivary glands in the major bronchi) (see Haagensen et al., 1986, supra; Mazoujian et al., *Am. J. Pathol.*, 110:105–112 (1983)). The biological purpose of apocrine cells secreting GCDFP-15 remains obscure. Recent data has shown that breast cell lines exposed to GCDFP-15 in the culture medium results in an enhancement in their growth rate (Cassoni et al., *Int. J. Cancer*, 60:216–220 (1995)). The protein does have a binding affinity for fibrinogen and is transported in blood bound to fibrinogen (Haagensen et al., 1990, supra). However, no enzymatic effect of GCDFP-15 on fibrinogen has been determined, thus far, and its purpose of binding to fibrinogen has not been established.

The secretion of GCDFP-15 has been shown to be regulated by various hormones both in vivo and in vitro (see Chalbos et al., *Cancer Res.*, 47:2787–2792 (1987); Simard et al., *Mol. Endocrinology*, 3:694–702 (1989); Dejardin et al., *J. Mol. Endocrinology*, 7:105–112 (1991); and Haagensen et al., *Br. Cancer Res. Treat.*, 23:77–86 (1992)). Androgens markedly enhance the excretion of GCDFP-15 from both the T47D and ZR75 breast cancer cell lines. The secretory effects of androgens on GCDFP-15 have been shown to be due to increased mRNA synthesis as a primary mechanism (Simard et al., 1989, supra). Differences have been observed between the T47D cells and the ZR75 cells with regard to growth effects of various steroids compared to secretion effects on GCDFP-15. In the ZR75 cell line, a positive correlation has been demonstrated between increased GCDFP-15 secretion and decreased growth rates (Simard et al., 1989, supra). This has been shown in both directions, with androgens slowing growth while increasing GCDFP-15 secretion and estrogens enhancing growth while decreasing GCDFP-15 secretion.

In contrast, with the T47D cell line, androgens have been shown to enhance GCDFP-15 secretion while not appreciably effecting the growth rate (Haagensen et al., 1992, supra). Progestins slow T47D growth rate, while enhancing GCDFP-15 secretion. However, RU486, an antiprogestin, also slowed growth in the T47D cell line while markedly inhibiting GCDFP-15 secretion (Haagensen et al., 1992, supra). Thus, the interaction of various steroids on breast cancer cell lines with regard to GCDFP-15 secretion is complex, but does appear to have androgen-modulated enhancement as a central effect.

SUMMARY OF THE INVENTION

This invention is directed to a method of determining the risk of breast cancer development in a subject with active breast gross cystic disease wherein said subject has at least one aspirated cyst. At the time of cyst aspiration, the level of GCDFP-15 in the plasma is measured. An increased level of GCDFP-15 in the plasma indicates an increased risk of breast cancer development.

A subject having between one and nine aspirated cysts, and having a GCDFP-15 level of greater than 40 ng GCDFP-15 per ml of plasma at the time of cyst aspiration, has a 4.2 times greater risk of developing breast cancer than a normal subject not having active breast gross cystic disease. A subject having ten or more aspirated cysts, and having a GCDFP-15 level of greater than 40 ng GCDFP-15 per ml of plasma at the time of cyst aspiration, has a 7.1 times greater risk of developing breast cancer than a normal subject not having active breast gross cystic disease.

DETAILED DESCRIPTION OF THE INVENTION 135 patients with active breast gross cystic disease were studied for GCDFP-15 production and breast cancer development. These patients provided 7 ml samples of peripheral blood for measurement of GCDFP-15 at the time of cyst aspiration. None of these subjects had prior breast cancer. Active gross cystic disease (GCD) was confirmed by aspiration of breast cyst fluid.

Follow-up reports of breast carcinoma at later dates were confirmed by obtaining copies of pathology reports. Follow-up time for each patient was measured from the date of first blood sample obtained at the time of active GCD, to the date of diagnosis of breast cancer (12 patients), death (2 patients), or last contact (121 patients), whichever came first. The average follow-up time was 10.1 years.

This group of 135 patients contributed 214 blood samples at the time of breast cyst aspiration. One hundred contributed a single sample and 35 contributed from 2 to 7 samples, taken at the time of aspiration for GCD.

Blood samples were collected in EDTA anticoagulated vacutainer tubes and were processed to plasma, then frozen at 70° C. until analysis. The analysis of the plasma level of GCDFP-15 was performed by a two stage RIA (see Haagensen et al., 1979, supra; Haagensen et al., 1986, supra; and Haagensen et al., *Proc. Am. Assoc. Clin. Chem.*, 26:980 (1980)). Briefly, purified GCDFP-15 was radiolabeled with $^{125}$I using Iodogen as described by Freker et al., *Biochem. Biophys. Res. Comm.*, 40:849–857 (1978)). Specific activity obtained was approximately 20 uCi/μg protein. For the two stage RIA, 100 μl of a specific rabbit anti-GCDFP-15 antiserum (diluted at 1/5000 in 0.01 M sodium azide containing 1 mg/ml bovine serum albumin) was added to 50 μl of the test plasma sample in an assay tube containing 800 μl of assay buffer (0.01M sodium azide with 1 mg/ml BSA). The reaction was allowed to incubate at room temperature overnight. The next morning, 100 μl of a solution of the $^{125}$I GCDFP-15 diluted to contain approximately 4 ng of the labeled protein was added. The assay tubes were gently vortexed, and then incubated for four hours at room temperature. The assay was terminated by the addition of 500 μl of a 1% solution of goat-anti-rabbit antibody attached to a solid support matrix of Kynar (see Haagensen et al., 1980, supra; and Newman et al., *Clin. Chem.*, 35:1743–1746 (1989)). The assay tubes were reacted for ten minutes and then centrifuged at 2000 rpm for 15 minutes. The supernatants were decanted and the pellets were counted in a Packard-Prias gamma counter.

An inhibition curve was developed from 0 to 5 ng of GCDFP-15, with the 5 ng point measuring approximately 10% of added counts. This standard curve measured from 0 to 100 ng/ml of GCDFP-15 for a 50 μl plasma sample. Plasma samples with blood levels of GCDFP-15 above 100 ng/ml were diluted in horse plasma and then reassayed in 50 μl aliquots. All plasma samples were assayed in duplicate with any duplicate sample having a variation of greater than ±2% being reassayed. This assay has a sensitivity of ±5 ng/ml of GCDFP-15 and an interassay CV of ±7%.

For data analysis, the plasma levels were grouped into three categories: normal (less than 40 ng GCDFP-15/ml plasma), midly elevated (40–49 ng/ml), and markedly elevated (50 ng/ml or greater). These ranges were chosen empirically on the basis of prior work on GCDFP-15 blood levels in a large sample of normal women (see Haagensen et al., 1986, supra; and Haagensen et al., 1990; supra. The total numbers of breast gross cysts confirmed by aspiration for the study group of 135 patients with GCD are shown in Table 1, below.

TABLE 1

Breast Gross Cystic Disease
Confirmed by Aspiration of Cyst Fluid

| Number of Aspirated Cysts | Number of Patients in Study |
|---|---|
| 1 | 13 (9.6%) |
| 2–9 | 59 (43.7%) |

TABLE 1-continued

Breast Gross Cystic Disease
Confirmed by Aspiration of Cyst Fluid

| Number of Aspirated Cysts | Number of Patients in Study |
|---|---|
| ≧10 | 63 (46.7%) |
|  | 135 (100%) |

The relationship between the total number of aspirated cysts and GCDFP-15 blood level is shown in Table 2, below. In order to maintain comparability among patients, patients are categorized according to their initial value of GCDFP-15. There is a slight, but not statistically significant, inverse association between number of aspirated cysts and blood level of GCDFP-15. As can be seen in Table 2, among women with only one aspirated cyst, 77% had GCDFP-15 plasma levels in the normal range and 23% had elevated levels. GCDFP-15 plasma levels were in the normal range in 59% of women with 10 or more aspirated cysts, and were elevated in the remaining 41%.

TABLE 2

Total Number of Aspirated Breast Cysts Versus Plasma Level of GCDFP-15 in the First Blood Sample Concurrent with Aspiration

| Number of Aspirated Cysts | Number of Patients | Percentage of Patients with GCDFP-15 Plasma Levels in ng/ml | | | |
|---|---|---|---|---|---|
| | | <40 | 40–49 | ≧50 | Total |
| 1 | 13 | 77% | 0 | 23% | 100% |
| 2–9 | 59 | 66% | 14% | 20% | 100% |
| ≧10 | 63 | 59% | 12% | 29% | 100% |
| Total | 135 | 64% | 12% | 24% | 100% |

Among the study group of 135 women, 12 developed initial carcinoma of the breast during the follow-up period. Ten of the cancers developed in women who had contributed a single blood sample, and two in women who had contributed serial (several) samples. The elapsed time between entering this study and developing carcinoma ranged from less than one year to 15 years.

The correlation between elevated plasma levels of GCDFP-15 and increased risk of developing breast cancer is shown in Table 3, below. As part of this analysis, the follow-up for the 35 patients with serial blood samples was allocated to blood level groups according to their highest last-known value. For example, one patient contributed a blood sample at age 40, which had a GCDFP-15 plasma level of 46, and another blood sample was contributed two years later, with a plasma level of 77. At the time of last contact, there was no known cancer. Two years of this patient's follow-up showed mildly elevated blood levels, and 9 years showed markedly elevated blood levels. Eight of the 35 patients who provided serial blood levels changed categories in this way.

TABLE 3

Relative Risk of Developing Breast Cancer
As Determined by Highest Prior Plasma Level of
GCDFP-15 By Total Number of Aspirated Breast Cysts

| Plasma Level of GCDFP-15 | Numb. Pts | Numb. Br.Ca. | Relative Risk | | Numb. Pts | Numb. Br.Ca. | Relative Risk | |
|---|---|---|---|---|---|---|---|---|
| <40 ng/ml | 49 | 2 | 1.8 | | 37 | 2 | 2.0 | |
| 40–49 ng/ml | 9 | 1 | 6.5 | } 4.2 | 11 | 2 | 7.1 | } 7.1 |
| ≦50 ng/ml | 16 | 1 | 3.1 | | 21 | 4 | 7.2 | |
| Study Group Total | 74 | 4 | 2.5 | | 69 | 8 | 4.4 | |

The risk of developing breast cancer is increased among women with several aspirated cysts. Therefore, data concerning cancer risk are shown separately according to whether or not the patient had a history of 10 or more breast cyst aspirations. In considering risk of breast cancer, it is also important to control for differences among groups in follow-up time, ages and calendar years of exposure. This was accomplished by calculating the relative risks of developing breast cancer for each group, that is, the ratios of the number of women in the group who developed breast cancer, to the number that would have been expected of normal women according to incidence rates from the Connecticut Tumor Registry for comparable ages and calendar years of exposure.

Table 3 shows that regardless of the total number of aspirated breast cysts, women with elevated levels of GCDFP-15 develop breast cancer at substantially higher rates than do women with normal blood levels of GCDFP-15. For women with fewer than 10 aspirated breast cysts, the relative risk among those with elevated blood levels of GCDFP-15 was 4.2, as compared to a relative risk of 1.8 for women with normal GCDFP-15 range blood levels. The difference in relative risks was more marked among women who had 10 or more aspirated breast cysts: 7.1 for those with elevated blood levels of GCDFP-15, versus 2.0 for those with normal GCDFP-15 range blood levels.

The last row of Table 3 shows the overall relative risk of developing breast cancer among women in the group of 135 women studied. For those women with fewer than 10 aspirated breast cysts, the risk is 2.5 times higher than for normal women. For those women with 10 or more aspirated breast cysts, the risk is 4.4 times higher than for normal women. These results correlate with breast cancer development risks determined by cyst aspiration studies performed in a study of 1770 patients with GCD (see Bodian et al., *Cancer Det. Prev.*, 16:7–15 (1992)).

The data presented herein indicate that blood levels of GCDFP-15 in women with active breast cystic disease distinguish subgroups with differing degrees of risk for developing breast carcinoma. Women with active breast gross cystic disease, as demonstrated by breast cyst aspiration, who also had an elevated GCDFP-15 blood level above 40 ng/ml, were at an increased relative risk for breast cancer development (Table 3). The degree of this increase in relative risk related to the degree of active gross cystic disease clinically in that it was higher in women who had developed 10 or more breast cysts. In this subgroup the increase in relative risk was elevated 7.1 fold, and was similar in degree to the increase in relative risk seen with the occurrence of atypical epithelial hyperplasia (Dupont et al., *New England J. Med.*, 312:146–151 (1985)), or with lobular carcinoma in situ (Bodian et al., *Epidemiological Reviews*, In Press (1995)). Since breast gross cystic disease is clinically much more common than either atypical epithelial hyperplasia or lobular carcinoma in situ (see Bodian et al., 1992, supra; and Bodian et al., *Cancer*, 71:3896–3907 (1993)), the measurement of GCDFP-15 blood levels is an important evaluation step in breast cancer risk assessment.

It is likely that GCDFP-15 blood level reflects both a secretory signal to apocrine metaplastic breast tissue and the amount of apocrine tissue present which can respond to the secretory signal. Both of these changes, jointly, appear to correlate with an increased susceptibility for breast cancer development. The use of blood levels of GCDFP-15 to reflect risk for breast cancer development opens new pathways into better understanding of this disease process and methods to alter this risk.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method of determining the risk of breast cancer development in a subject with active breast gross cystic disease having between one and nine cysts, comprising determining the level of GCDFP-15 in the plasma of said subject at the time of aspirating said cysts, an increased level of GCDFP-15 in the plasma indicating an increased risk of breast cancer development in said subject.

2. The method of claim 1 wherein said increased level of GCDFP-15 is greater than 40 ng GCDFP-15 per ml plasma.

3. The method of claim 2 wherein said increased risk of breast cancer development is 4.2 times greater than the risk of breast cancer development in a normal subject not having active breast gross cystic disease.

4. The method of claim 1 wherein said breast cancer is breast carcinoma.

5. The method of claim 1 wherein said subject has had no prior breast cancer.

6. A method of determining the risk of breast cancer development in a subject with active breast gross cystic disease having ten or more cysts, comprising determining the level of GCDFP-15 in the plasma of said subject at the time of aspirating said cysts, an increased level of GCDFP-15 indicating an increased risk of breast cancer development in said subject.

7. The method of claim 6 wherein said increased level of GCDFP-15 is greater than 40 ng GCDFP-15 per ml plasma.

8. The method of claim 7 wherein said increased risk of breast cancer development is 7.1 times greater than the risk of breast cancer development in a normal subject not having active breast gross cystic disease.

9. The method of claim 6 wherein said breast cancer is breast carcinoma.

10. The method of claim 6 wherein said subject has had no prior breast cancer.

* * * * *